United States Patent [19]
Taylor et al.

[11] Patent Number: 6,030,386
[45] Date of Patent: Feb. 29, 2000

[54] SIX AXIS EXTERNAL FIXATOR STRUT

[75] Inventors: Harold S. Taylor; J. Charles Taylor, both of Memphis, Tenn.

[73] Assignee: Smith & Nephew, Inc., Memphis, Tenn.

[21] Appl. No.: 09/131,605

[22] Filed: Aug. 10, 1998

[51] Int. Cl.[7] .................................................. A61B 17/60
[52] U.S. Cl. ............................................. 606/56; 606/54
[58] Field of Search .................................. 606/54, 55, 56, 606/57, 58, 59

[56] References Cited

U.S. PATENT DOCUMENTS

| | | |
|---|---|---|
| 2,055,024 | 9/1936 | Bittner, Jr. . |
| 3,941,123 | 3/1976 | Volkov et al. . |
| 3,985,127 | 10/1976 | Volkov et al. ............................ 606/55 |
| 4,033,340 | 7/1977 | Kalnberz . |
| 4,100,919 | 7/1978 | Oganesyan et al. . |
| 4,112,935 | 9/1978 | Latypov et al. . |
| 4,127,119 | 11/1978 | Kronner . |
| 4,308,863 | 1/1982 | Fischer . |
| 4,365,624 | 12/1982 | Jaquet ........................................ 606/56 |
| 4,541,422 | 9/1985 | de Zbikowski . |
| 4,554,915 | 11/1985 | Brumfield . |
| 4,889,111 | 12/1989 | Ben-Dov ................................... 606/54 |
| 4,928,546 | 5/1990 | Walters . |
| 5,062,844 | 11/1991 | Jamison et al. . |
| 5,180,380 | 1/1993 | Pursley et al. ............................ 606/56 |
| 5,702,389 | 12/1997 | Taylor et al. .............................. 606/56 |
| 5,797,908 | 8/1998 | Meyers et al. ............................ 606/54 |

FOREIGN PATENT DOCUMENTS

| | | |
|---|---|---|
| 2 576 774 | 8/1986 | France ........................... A61B 17/60 |
| 2 756 025 | 11/1996 | France . |
| WO 96/26678 | 9/1996 | WIPO ............................. A61B 17/60 |

OTHER PUBLICATIONS

Nicholas P. Chironis "Mechanisms & Mechanical Devices Sourcebook" pp. 366,367, McGraw–Hill, Inc., 1991.

Techniques in Orthopaedics, Basic Ilizarov Techniques, vol. 5 No. 4, Dec. 1990.

"The Ilizarov External Fixator, General Surgical Technique Brochure," 1988.

"Monticelli Spinelli External Fixation System," pp. 1–28, Pfizer Hospital Products Group, 1991.

Gavriill A. Ilizarov "Transosseous Osteosynthesis—Theoretical and Clinical Aspects of the Regeneration and Growth of Tissue," Springer–Veriag, 1992.

A.S.A.M.I. Group, "Operative Principles of Ilizarov—Fracture Treatment, Nonunion Osteomyelitis, Lengthening Deformity Correction," Medi Surgical Video, 1991.

M.A. Catagni, V. Malzev–A. Kirienko, "Advances in Ilizarov Apparatus Assembly—Fracture Treatment, Pseudarthroses–Lengthening Deformity Correction," Medicalplastic srl, 1994.

*Primary Examiner*—Michael Buiz
*Assistant Examiner*—Daphna Shai
*Attorney, Agent, or Firm*—Pretty, Schroeder & Poplawski

[57] ABSTRACT

An orthopedic fixation device in which two or more translation members are secured to adjacent tissue segments for reorientation relative to each other. The device includes telescopically adjustable struts that can be secured to base members by connectors that permit movement of the struts relative to the base members. Rotation of the struts is possible about three axes that intersect at a single coincident point of universal rotation.

24 Claims, 6 Drawing Sheets

SIX AXIS EXTERNAL FIXATOR STRUT

BACKGROUND OF THE INVENTION

The present invention relates to orthopedic devices, and more particularly to devices know as external fixators or skeletal fixators. These devices are used, as an alternative to plaster casts or a combination of surgically implanted screws, pins and plates, to reposition two tissue segments, e.g. bone elements, relative to each other. More specifically, the invention relates to an adjustable strut for use as a component of such a fixator. Additional background information relating to such devices can be found in U.S. Pat. No. 5,702,389, having the same inventors.

Skeletal injuries or conditions are sometimes treated with an external fixator that is attached to the boney skeleton with threaded and/or smooth pins and/or threaded and/or smooth or beaded wires. External fixators may be utilized to treat acute fractures of the skeleton, soft tissue injuries, delayed union of the skeleton when bones are slow to heal, nonunion of the skeleton when bones have not healed, malunion whereby broken or fractured bones have healed in a malposition, congenital deformities whereby bones develop a malposition, and corrective bone lengthening, widening, or twisting.

External fixators vary considerably in design and capabilities, and may include multiple or single bars or rods, and a plurality of clamps for adjustably securing the bars to pins or wires which are, in turn, joined to the boney skeleton. The pins or wires may extend completely through the boney skeleton and protrude from each side of the limb, or may extend through the boney skeleton and protrude from only one side of the limb. Pins which extend completely through the boney skeleton and protrude from both sides of a limb are commonly referred to as "transfixation pins." Pins which extend through the boney skeleton and protrude from only one side of the limb are commonly referred to as "half pins."

External fixators may be circumferential, encircling a patient's body member (e.g., a patient's leg), or may be unilateral, extending along one side of a body member. More than one unilateral external fixator can be applied to the same portion of the patient's body member. Materials from which fixators are constructed vary, including metals, metal alloys, plastics, composites, and ceramics, as is known to those skilled in the art. External fixators also vary considerably in their ability to accommodate different spatial relations between the relevant tissue segments.

One of the more commonly used types of external fixators was described by G. A. Ilizarov during the early 1950's. The Ilizarov system includes two or more rings or "halos" that encircle a body member, connecting rods extending between the two rings, transfixion pins that extend through the patient's boney structure, and connectors for attaching the transfixion pins to the rings. Use of the Ilizarov system to address problems of angulation, translation and rotation is disclosed in "Basic Ilizarov Techniques," *Techniques in Orthopaedics®*, Vol. 5, No. 4, December 1990, pages 55–59.

The Ilizarov system allows a physician to reorient one tissue fragment with respect to another along six axes in an acute motion. However, this system is disadvantageous in that it utilizes hinges and translation mechanisms which must be specifically constructed for a given case. Considerable planning, fabrication and preparation is required to use the device because it utilizes different mechanisms depending on the translational or rotational corrections a bone is required to undergo. Moreover, it requires that the physician loosen one or more clamps, apply corrective motion manually, and then retighten the clamps to hold the fragments stably each time a new or adjusted bone position is required. Aside from the disadvantages of inconvenience and imprecision, this system has the further undesirable effect of necessarily subjecting the skeletal tissues to abrupt motion, sometimes along an indirect path.

The mathematics describing the positional relations of tissue segments are best illustrated by the "Chasles axis theorem." Chasles recognized that the complex repositioning of an object with respect to six axes (three rotational and three translational) could be duplicated by the rotation of a threaded nut along a threaded shaft. This theoretical shaft is oblique to an arbitrary reference axis. The offset from the center of the shaft (i.e., the thickness of the imaginary shaft) will satisfy two translational components and the pitch of the thread satisfies the third translation. Rotation around the oblique shaft is the equivalent to a combination of three orthogonal rotations. This modeling of six repositioning elements serves as a useful model for understanding orthotic deformity correction where a skeletal element must be translated and rotated to restore its correct position. Specifically, by taking advantage of this oblique Chasles axis, all three mal-rotations and all three mal-transitions of a deformity can be corrected simultaneously.

The essential elements of a more recently developed device (referred to hereinafter as the earlier Taylor device) were described in a publication entitled "The Taylor Spatial Frame Fixator" by Dr. J. Charles Taylor M.D. (see also U.S. Pat. No. 5,702,389). This fixator, which utilizes the Chasles axis theorem, consists of two base elements, usually rings or partial rings, connected by at least six telescopic struts. At least three connection points are selected on each ring, and the struts are connected to connection points in series (thereby defining the effective plane that is manipulated by the struts).

The earlier Taylor device manipulates the adjacent bone tissues through the predicted effect an adjustment of each of the six struts will have on the base members. Through translation and rotation analysis of one of the tissue segments relative to the other, a desired position of the base members can be calculated. Geometric principles are applied to the initial and final position of the strut ends to calculate the final strut length.

The earlier Taylor device can best be used in one of two modes. In the first mode, known as the chronic method, the base members mimic the deformity in the bone tissues before being brought back the a neutral position. In other words, after an initial aligned and parallel position for the base members is determined, one of the base members is translated in the same direction, and rotated about the same point, as the deformed bone member has been translated and rotated from the target position. The fixator is then attached to the bone segments and brought back to its initial aligned position, thereby reorienting the bone members as desired. The second mode of operation, the acute method, works in a manner essentially opposite to the chronic method. The device is attached to the tissue segments in a neutral position. Calculations are then made to determine the translational and rotational requirements for the base members to mirror the bone tissue deformity. Thus when the base members are brought to this mirroring position, the tissue segments will be in alignment, with the base members in an unaligned position.

The connecting interface between each strut and the end plates in the earlier Taylor device consists of a captured bifurcated ball joint. This connection provides four degrees of freedom (i.e., three orthogonal degrees of strut rotation relative the base member and one degree of rotation about an axis perpendicular to the face of each hemisphere). Adjustment is accomplished with a turnbuckle-style shaft which is threaded about a rod at either end, with the direction of the threads at one end being reversed relative the other end. Thus rotation of the turnbuckle causes the rods, and thus the base members, to expand or contract.

Despite the important advances embodied in the earlier Taylor device, its performance could be more advantageous in some situations. The captured ball system is not ideal for application to an orthopedic fixator because it tends to bind as the fixator is forced to deform beyond certain limits. In other situations, the rotation of the captured ball relative the strut could cause small changes in the length of the strut. Moreover, the turnbuckle style strut used in the earlier Taylor device is free to rotate about the adjustment rods, thereby creating a risk that the relative position of the base members can drift from the intended position.

The earlier Taylor device is also relatively difficult to use in situations in which the struts must be removed. In some cases the translation of the tissues will cover a considerable distance or angle, requiring commensurate extension or retraction of the struts. Thus, it is sometimes necessary to replace one or more struts with struts of a different size during a clinical procedure. Moreover, even after the connector has been disassembled, the permanent indications of position on the earlier Taylor device make it more difficult to remove and replace struts, since each strut is designed for a specific position on the frame.

When using the earlier Taylor devices, it is sometimes difficult to determine the effective length of the strut. The device does provide slots through the side of the turnbuckle through which the position of the internal rod can be seen. However, since the shaft on the turnbuckle has to be rotated to see in the slot, the act of checking the position can result in an undesired or unintended change in position.

In light of the foregoing, it will be appreciated that there is still a need for an improved telescopically adjustable strut for use with an external orthopedic fixator. Ideally, the strut should not bind against the base members when the components form relatively sharp angles, it should visibly indicate the effective length of the struts without requiring that the length be altered to observe the indication, it should be capable of rotating axially without altering its effective length, it should indicate the strut's position on the fixator yet remain interchangeable with other fixators at other positions on the device, and it should be axially adjustable without requiring clamps yet should not permit drift from the desired effective length.

SUMMARY OF THE INVENTION

This invention pertains to an improved telescopically adjustable strut to be used in conjunction with an external orthopedic fixator. Each such strut is used with a multitude of other struts of similar construction to position two or more base members relative to each other, thereby positioning two tissue segments, such as bone fragments, that are each secured to one of the base members. In combination with other features described below, this improved strut provides increased flexibility, adaptability, precision and convenience. Moreover, these objectives are accomplished with a design that is simple, reliable and relatively inexpensive to manufacture.

The primary structural components of the strut include a hollow shaft, a threaded rod which telescopically extends into the one end of the shaft, an adjustment nut which is rotatably joined to the shaft and threaded onto the rod, and a connector at each end of the strut that secures the strut to the adjacent base members.

An important feature of this invention is the connectors which permit the strut to rotate axially without binding or altering the relative orientation of the base members. Each connector includes a joint fixed to the end of the rod or shaft that permits two orthogonal degrees of rotation. A third degree of rotation, orthogonal to the axes of one of the first degrees, can be provided through a fastener by which the connector is fixed to the adjacent base member. Thus the strut is free to rotate relative the base member in all three directions.

The present invention provides a single point of coincident rotation at which all of the axes of rotation in each connector meet. This feature allows axial rotation of the body of the strut between the connectors without regard to the orientation of the strut relative the base members. Moreover, the existence of a single point of coincident rotation at either end of the strut allows the strut to rotate axially in any orientation without altering the relative positions of the base members.

Another feature of the present invention is the provision of a telescopic strut, which preferably allows continuous non-discrete adjustments in length without sacrificing the stability of the strut while in a fixed position. The invention also provides an easily removable fastener for joining the struts to the base members. Thus the strut can safely be removed from the fixator to replace it with one of a different size during a clinical application. According to the present invention, the strut may be fastened to the base member in such a way that it may be removed from the fixator entirely without adjusting its effective length.

The present invention also provides a telescoping strut in which a rod traverses through a shaft without rotating axially relative to the shaft. The rotation of an adjustment member relative the rod and shaft adjusts the relative axial positions of the rod and shaft.

The present invention can also provide a readily visible indication of the length of the strut. This indication can be obtained, in a preferred manner, by observing the position of a portion of the rod through an opening hole in the side of the shaft. The present invention can provide for and facilitate measured, incremental extension of the strut that corresponds with the common medical practice of translating bone fragments a maximum of one millimeter per day.

An adjustment nut can be secured to the shaft while preserving the ability of the nut to rotate relative to the shaft. Rotation of the nut relative the shaft and the rod can cause the strut to extend or contract.

The invention can provide a detent locking mechanism that prevents accidental or floating adjustment of the strut length. This mechanism can be activated without clamps or bindings. It can be released upon application of a predetermined torque to the adjustment member relative the shaft and rod assembly. The detent mechanism can be made to remain engaged despite the application of torque to the adjustment member relative the base members. Thus the application of torque on the adjustment member without securing the shaft and rod assembly relative the adjustment member will simply cause the strut to rotate about the connectors without changing length. The detent mechanism can advantageously be located within the juncture between the adjustment member and the shaft.

The invention allows the strut to be identified relative to its position on the base members and relative to the other strut members of the fixator. A removable identification tag can be included which can be interchanged with similar identification tags from other struts. The identification tag can also provide a color-coded indication of the position of each strut relative the base members and relative the other struts. A universal strut thus can be provided that is usable at any location on the fixator.

DESCRIPTION OF THE PREFERRED EMBODIMENTS

Figure 1:
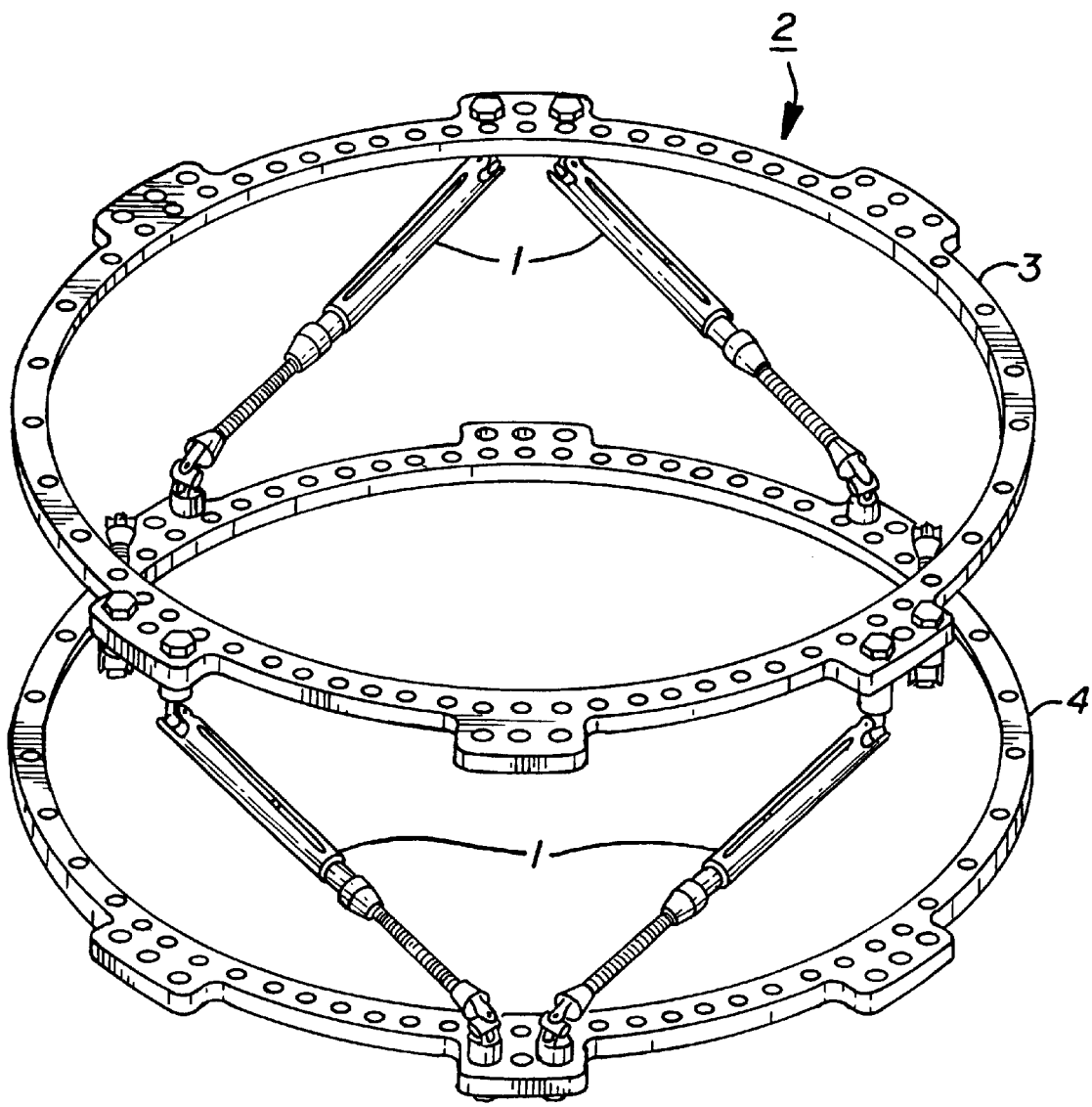
FIG. 1 is a perspective view of a preferred embodiment of this invention showing six struts placed in symmetrical positions about two base members of an external fixator.
Figure 7A:
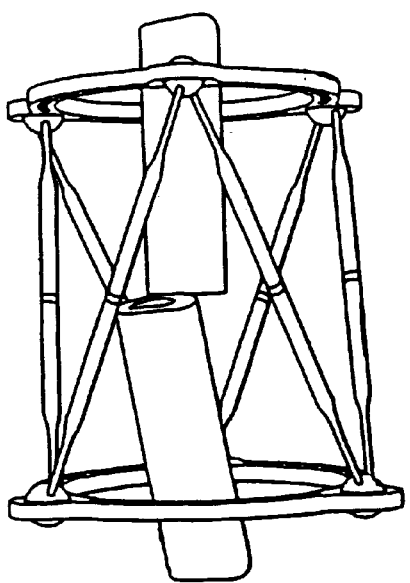
FIG. 7 illustrates the steps involved in a first unique preferred method of using an external fixation device, and include a perspective view of the apparatus before (7a) and after (7b) the External Fixator struts of the present invention have been adjusted to correct a deformity.

Telescopic struts 1 are to be used in combination with an external orthopedic fixator 2, generally illustrated in the accompanying FIGS. 1, 7, and 8. This exemplary external fixator 2 is part of a unique orthopedic fixation system designed for treating a variety of fractures, nonunions and malunions of skeletal tissue segments, such as bone fragments.

The external fixator 2 includes two rings or partial rings that form base members 3,4 connected by six telescopic struts 1. Adjustment of each strut length alters the orientation of the base members relative to each other. Thus, if a tissue segment is secured to each base member, the relative positions of the tissue segments can be changed and manipulated by adjusting the lengths of the struts.

Figure 7B:
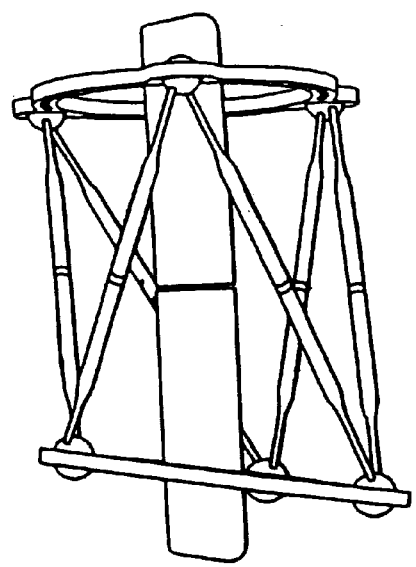
Figure 8A:
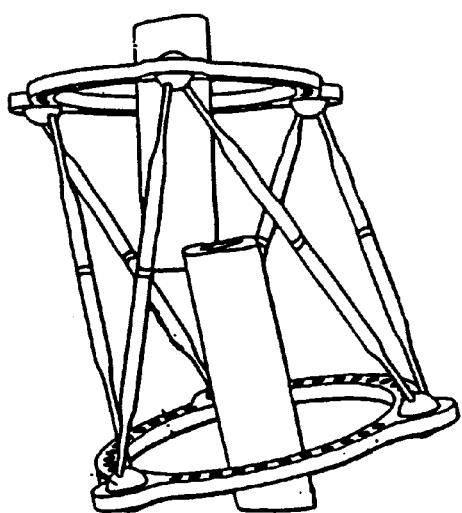
FIG. 8 illustrates the steps involved in a second unique preferred method of using an external fixation device, and include a perspective view of the apparatus before (8a) and after (8b) the External Fixator struts of the present invention have been adjusted to correct a deformity.
Figure 8B:
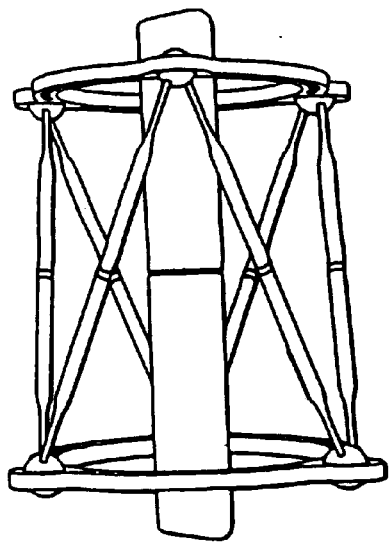

When the chronic method of deformity correction is used (see FIG. 7), the fixator 2 is moved from an initial position in which the base members are aligned in parallel planes, to a position that mimics a deformity and then attached to the tissue segments (FIG. 7a), and then the struts are returned to a predetermined neutral position to realign the tissue segments (FIG. 7b). When the acute method of operation is used, the base members are attached to the bone fragments in a predetermined aligned position (FIG. 8a), and then adjusted to mirror the deformity, thereby bringing the fragments into alignment (FIG. 8b). When either method is used, the struts can be adjusted in increments over a specified period of time to slowly bring the bone fragments into the desired alignment.

A mathematical correlation between the positions of the tissue segments may be used to predict the relative movement of the base members 3,4 required to realign the tissue segments. After the desired position of the base members has been predetermined, geometric analysis of the initial and final positions of the struts can be used to calculate the target lengths for the struts. Adjustment of the struts to this target length will bring the tissue segments into the desired alignment. (See U.S. Pat. No. 5,702,389).

Preferably, the connecting prints between the struts 1 and the base members 3 or 4 all lie on a single plane relative to each base member. The connections on each base member are preferably symmetrical. Such symmetry is not entirely necessary for the base members to move in six degrees, or for that matter for the fixator 2 to function properly. However, adjustment of the tissue segments requires in part that the positions of the connectors be measured relative to the tissue segments and a selected coordinate system. Therefore, it simplifies the process greatly if similar calculations can be made for each connection point.

Figure 2:
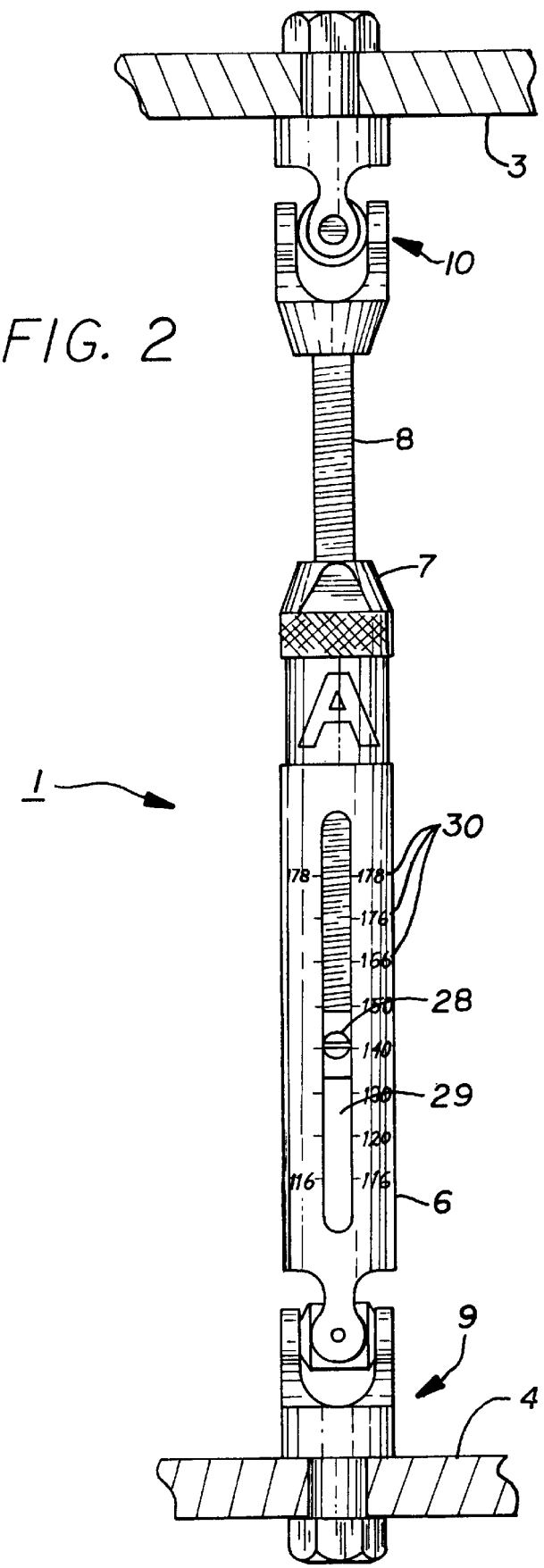
FIG. 2 is a plane view of a preferred embodiment of the strut of the Fixator of FIG. 1, with the base members partially in cross section at either end.

All of the struts 1 on a fixator device 2 are preferably similar in construction to one another, thereby making the struts interchangeable. Referring in particular to FIG. 2, a preferred embodiment of the strut is illustrated. The primary structural components of this strut 1 include a hollow shaft 6, an adjustment nut 7, a threaded rod 8 which mates with the adjustment nut, a connector 9 joined to the end of the shaft, and a connector 10 joined to the end of the rod.

Figure 3:
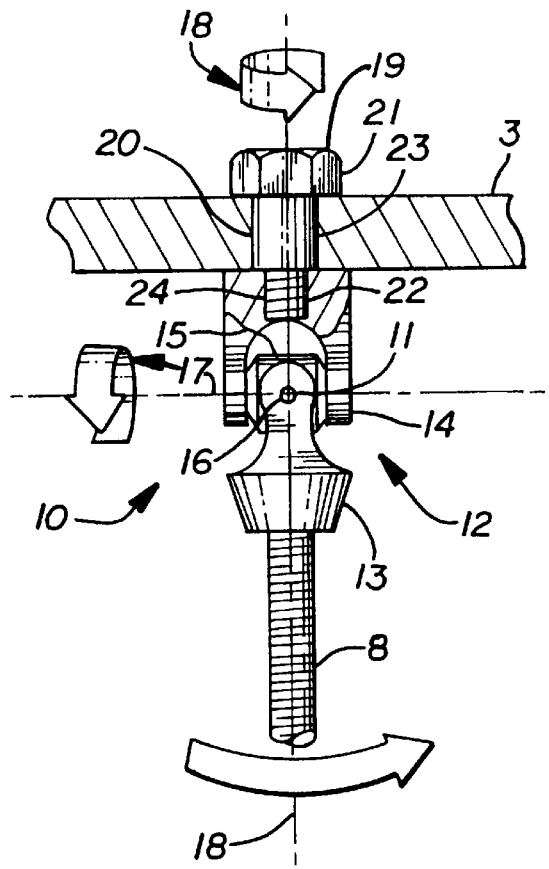
FIG. 3 is an enlarged planar view of the connector strut of FIG. 1 indicating the axes of rotation and the single coincident point of rotation at the intersection of the axes.

Referring specifically to the connector design illustrated in FIG. 3, each end of the strut 1 is free to rotate about three orthogonal axes relative the adjacent base member. Moreover, this axial rotation is possible without altering the effective length of the strut. This is accomplished by providing a connector mechanism 10 that orients all three axes of rotation about a single point of coincident rotation 11.

The preferred embodiment utilizes U- joints 12 fixed to the end of the strut 1 to define two of the rotational axes. Each U-joint 12 includes a first flanged portion 13 attached to the of the strut (i.e. the end of the rod 8 as illustration of FIG. 3, and the end of the shaft 6 on the other end, not illustrated). A second flanged portion 14 is located facing toward the first flanged portion 13, but it is rotated 90 degrees. Both pairs of flanges extend between the flanges of the adjacent flanged portion. Situated between all four flanges is an axial joint 15 which is rotatable about both a first axis 16 extending between the flanges of the first flanged portion, and about a second axis 17 extending between the flanges of the second flanged portion. Thus the flanged portions 13, 14 are free to rotate relative to each other about two orthogonal axes 16, 17.

A third axis of rotation 18 is defined at the end of each connector 9, 10 by a fastener 19 which secures the U-joint 12 to the adjacent base member 3 or 4. The fastener extends through an aperture 20 in the adjacent base member, but is not tightened enough to bind. Thus the U-joint is free to rotate about the fastener. This creates a third rotational axis of rotation 18 that is normal to the second rotational axis 17 and intersects both the first axis of rotation and the second axis of rotation at a common point, also known as the coincident point of universal rotation 11.

Figure 6:
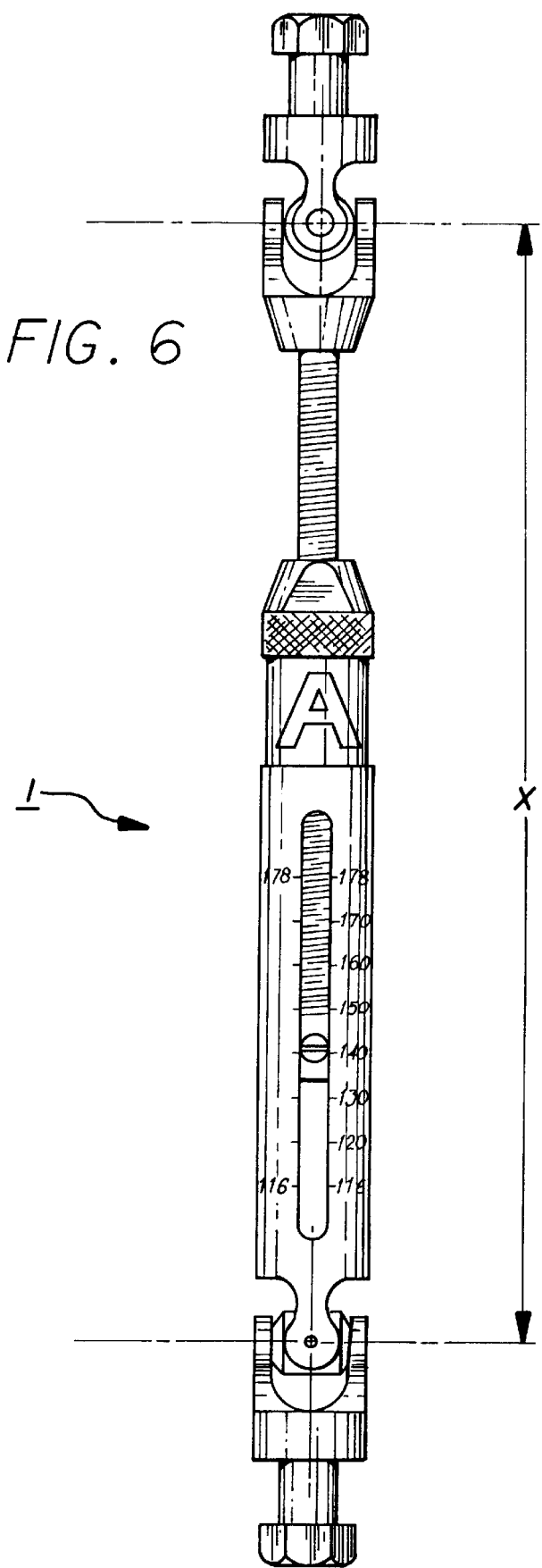
FIG. 6 is a plane view of the strut indicating the effective length of the strut between the coincident points of rotation at either end.

The coincident points of universal rotation 11, located at either end of the strut 1, provide a significant improvement in the performance for the fixator 2 because they enable the strut to rotate axially without binding or changing length. Thus the axial angular orientation of the strut is free to float and rotate without risk of injury to the attached tissue segment. Moreover, having a coincident point of rotation at either end of the strut is important to accurately calculate the required lengths of the struts to orient the base members 3,4 into a target position. As illustrated in FIG. 6, the length between the coincident points of rotation, x, is the effective strut length preferably used in the calculations. The locations of the points of coincident universal rotation are used as the references from which the base members 3, 4 are translated and rotated to mimic, or mirror, the deformity between the tissue segments. If the three axis axes of rotation 16, 17, 18 did not meet at a single point, the geometric effect that the strut lengths have on the base member would vary depending on the angle between each strut and the adjacent base member. Theoretically, the repositioning calculations would still be possible given the exact position of each rotational axis. However, these calculations would be very complex and difficult, introducing more possibilities for error.

As illustrated in FIG. 3, the fastener 19 has a head 21 at one end, a threaded portion at the other end 22, and an unthreaded shank 23 in the middle. Connection of the strut 1 to a base member 3,4 is accomplished by extending the fastener through aperture 20, screwing the threaded portion 22 into a threaded receptacle 24 in the adjacent U-joint 12. Ideally the fastener is a shoulder bolt as illustrated in FIG. 3. The fastener 19 will be rotatable in the aperture 20 if the shank 23 is longer than the depth of the aperture, and wider than the receptacle. Thus, when the fastener 19 is secured in the U-joint 12, there remains a sufficient allowance between the head 21 of the fastener and the bottom side of the U-joint to permit rotation of the strut about the axis of the fastener. Note, however, that care should be taken to keep close tolerances between the fastener and the adjacent base member, as a small variance at a near end of the strut can result in excessive play at the distant end of the strut.

It will be understood that the U-joint 12 could be arranged such that it rotates about the end of the rod rather than the adjacent base member. If the fastener 12 then rotates about the rod (or shaft at the end not illustrated in FIG. 3) with similar allowance as that available with a shoulder bolt, the same goal of three point rotation can be achieved. However, this arrangement is not preferred over the relatively simple application described above, in part because it adds to the number of components in the device.

In accordance with the modularity aspect of the invention, there is a need for the fasteners 19 to be removable so that the struts can be interchanged without altering the positions of the base members. Thus in the preferred method the fastener accomplishes two purposes. Moreover, since it is difficult to design a U-joint which will not bind at certain sharp angles, it is advantageous that the base of the U-joint can rotate around the fastener axis to avoid those angles.

An advantage of using connectors of the type described herein is that the struts 1 can readily be adapted to clinical situations requiring differently sized fixators. When a particular sized fixator is too large or small, or when a deformity correction requires that a strut be extended or compressed beyond its limits, the strut in question can simply be removed "mid-process" and replaced with a more suitably sized strut. It is for this reason that the fastener 19 is preferably removable from the backside of the base member 3,4, and the U-joint 12 preferably fits flush against the base member. The strut can then be removed without having to adjust its length. It is preferred that the struts be manufactured in at least three length ranges to optimize the capabilities of the fixator. Preferably the longest struts range from 170–280 millimeters, the medium struts should range from 116–178 millimeters, and the shortest struts should range from about 90–125 millimeters. A 1.5 to 2 centimeter overlap between sizes is most preferred.

Figure 4:
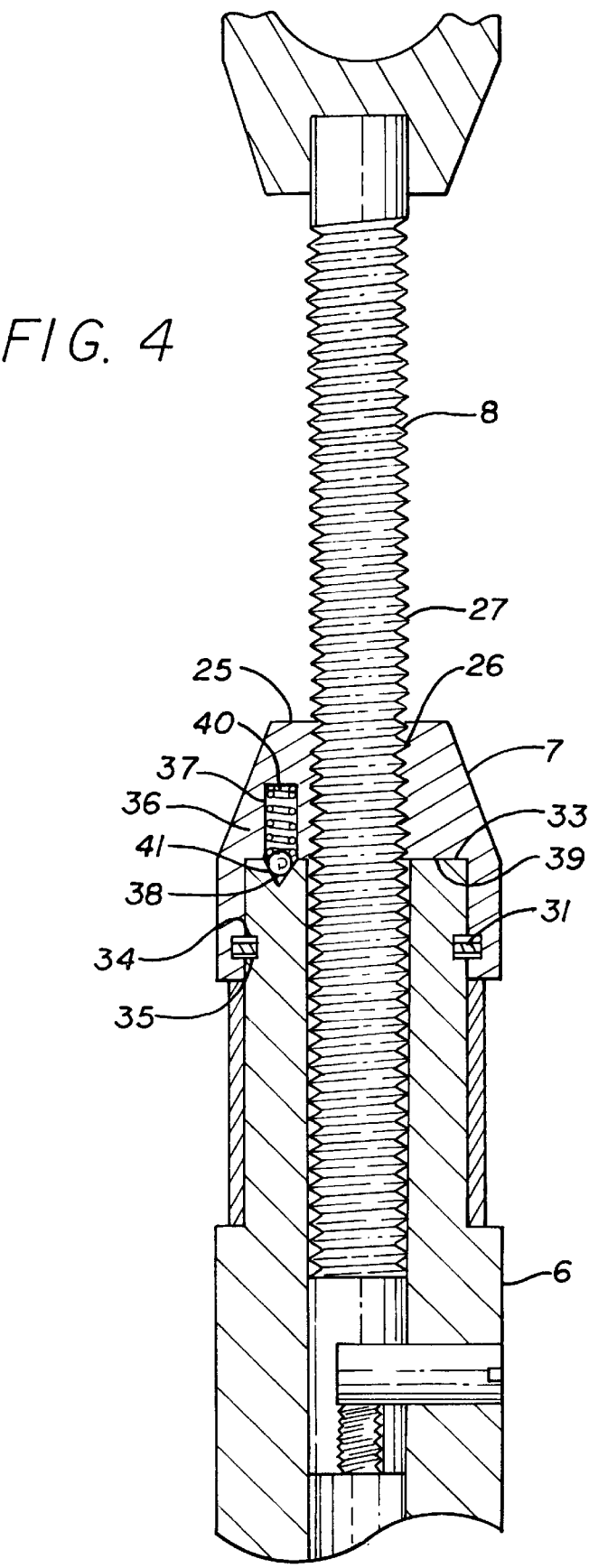
FIG. 4 is a fragmentary cross-sectional view of the strut, illustrating the relation between an adjustment nut and the telescoping sections of the strut, as well as the detent mechanism which holds the adjustment nut in position between axial settings.

Referring generally to FIG. 2, and specifically to FIG. 4, the preferred strut 1 has an externally threaded rod 8 which freely extends into the hollow shaft 16. An adjustment member in the form of a nut 7 is rotatably joined to the open end of the hollow shaft 6 and includes internal threads 26 which mate with the threads 27 on the rod. As described in more detail below, the adjustment nut 7 is free to rotate about the axes of the rod 8 and the hollow shaft 6, thereby providing a means for telescopically adjusting the axial positions of the rod relative to the shaft.

As shown in FIG. 2, an indicator of the relative position of the rod 8 to the shaft 6, and thus the effective length of the strut 1, is provided by a projection in the form of a pin 28 which is radially connected to the rod 8 near the end that extends into the shaft 6. A slot 29 is provided along the side of the shaft 6 so that the pin 28 travels along the slot, thereby permitting the pin to be seen from outside the shaft. A primary function of the pin 28 is to prevent relative axial rotation of the rod 8 and shaft 6. This is significant because the connectors 9,10 and corresponding points of coincident rotation 11 permit axial rotation of the rod 8 and shaft 6 at either end of the strut.

Graduation marks 30 are provided along side the slot 29 to indicate the position of the rod 8 relative to the shaft 6. This arrangement works particularly well in combination with the connectors 9,10 described herein because, no matter how the base members 3,4 are oriented relative to each other, the strut 1 can be rotated about the connectors to position the slot in the most visible position.

The graduation marks 30 are preferably calibrated in one millimeter increments, and preferably indicate the distance between the points of coincident rotation 11 at either end of the strut 1. It is also preferred that the graduation marks 30 indicate the lengths of the struts 1 as an absolute value, rather than the distance from some predetermined neutral position. However, the graduation marks do not necessarily have to be based on a traditional measuring system, or for that matter, indicate the effective length of the strut at all. For instance, the graduation marks could indicate the percentage of total rod extension, or daily increments for cases where the translation takes place over an extended period of time. Reference to a neutral position can be useful to set the base members at a predetermined "neutral" position, but it has been found beneficial to avoid specifying such a universal "neutral" position in order to encourage physicians to optimize the fixator for each case.

One of skill in the art will recognize that there are other methods for locking the relative rotational positions of the rod 8 and shaft 6 (e.g., a key in the shaft which engages a longitudinal groove in the rod, not illustrated), but the pin and slot method has been found to work particularly well because the pin 28 simultaneously provides a convenient indicator by which the strut length can be monitored. Moreover, the pin 28 limits compression and extension of the shaft to the extent that the pin will abut either end of the slot 29 upon full extension or contraction of the strut.

The adjustment nut 7 is rotatably fixed to the shaft 6 via a snap ring 31 illustrated in FIG. 4. The end of the shaft 6 extends partially into the interior of the adjustment nut where it abuts an inner wall 33 of the nut 7. An exterior annular groove 34 on the shaft abuts an interior annular groove 35 on the nut, and the snap ring 31 fits within both annular grooves. The snap ring 31 is also compressible to allow assembly, but once inside the adjacent grooves 34, 35 the snap ring expands radially outwardly thereby filling a portion of both annular grooves. Thus the adjustment nut can rotate about the snap ring without coming off the end of the shaft.

The length of each strut 1 may also be independently adjustable so that the position of the fixation device can be quickly changed from one position to another. This can be accomplished with a springed jaw mechanism (not illustrated) which engages (and releases) the threads of the nuts with those of the rod. When the jaws are open, the rod can be translated relative the shaft without rotating the nut. However, when the jaws are closed the engagement of the threads of the nut and the rod prevents such translation movement without rotation the adjustment nut. This ability to select between coarse or fine adjustments of the effective length can be particularly useful to bring the fixator relatively close to a desired point. From there the adjustment nut can be used to fine tune the related position of the base members.

A detent mechanism 36 is provided at the interface between the adjustment nut 25 and the shaft 6. Referring again to FIG. 4, the preferred configuration for the detent mechanism includes a first recess 37 formed in the adjustment nut and a second recess 38 formed in the end surface 39 of shaft 6 that remains in contact with the adjustment nut. Upon each revolution of the adjustment nut 7, the depressions come into alignment (as indicated in FIG. 4). When the depressions are aligned, a spring 40 located in the first depression 37 biases the ball 41 toward, and into engagement with, the second depression 38. Preferably the second depression is bounded by an annular inclined plane as indicated in FIG. 4, but the depression can also have squared edges, so long as diameter of the ball 41 is larger than the diameter or depth of the second depression.

The detent mechanism is released by applying a predetermined torque on the adjustment nut 25 sufficient to force the ball 41 to move out of the second depression 38 against the force of the spring 40. At that point the only hindrance to the rotation of the nut relative the shaft is the relatively low friction created by adjacent parts. Preferably, the force needed to overcome the locking effect of the detent mechanism 36 is greater than that required to rotate the strut 1 about the connectors 9,10. Thus an application of torque on the adjustment nut 25 without securing the relative rotation of the rod 8 or shaft 6 will simply cause the entire strut 1 to rotate. This free floating arrangement for the strut will help prevent undesired or unintentional adjustments.

Figure 5:
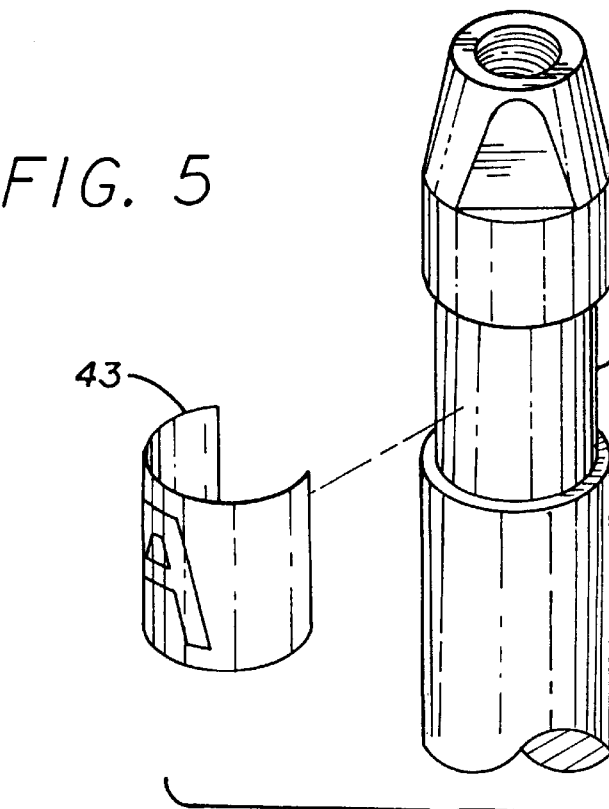
FIG. 5 is an exploded view of the strut illustrating the removal of the position indicator.

Referring to FIG. 5, the shaft 6 also preferably includes an annular recess 42 for the attachment of an identification clip or band 43. The identification clip 43 is resilient and encompasses more than 180 degrees of the recess 42 such that it will snap onto the recessed portion of the shaft and may be removed and transferred to another similarly designed strut where necessary.

To achieve a particular configuration of the mechanism, each of the six struts 1 must be set to a specific length depending on the predetermined coordinate system. Since the calculations will usually require that each strut have a different length, each strut should be distinctly identifiable to ensure that it is adjusted correctly. This identification can be accomplished with the use of removable identification clips 43 of different colors or alphanumeric indications as illustrated in FIG. 5. The transferability of the identification clips is valuable in cases in which a strut 1 must be replaced because it is broken, or of the wrong size, or where varying size struts are used on the same device and the struts must be rearranged. The removability of the identification clip 43 ensures that the struts are interchangeable.

Although the invention has been described in detail with reference only to certain embodiments, those skilled in the art will appreciate that various modifications can be made without departing from the spirit of the invention. With such possibilities in mind, the invention is defined with reference to the following claims.

We claim:

1. In combination with an orthopaedic external fixator having proximal and distal base members that can be manipulated relative to each other to position a first tissue segment relative to a second tissue segment, an adjustable strut comprising:

a telescopic body with a proximal end and a distal end;

a pair of connectors, one rotatably attaching the proximal end of the strut to the proximal base member and one rotatably attaching the distal end of the body to the distal base member, each of said connectors comprising:

a) a first pivot member joined to the adjacent end of the body;

b) a second pivot member pivotally joined to the first pivot member; and c) a third pivot member pivotally joined to the second pivot member and pivotally joined to the adjacent base member;

wherein the first pivot member is pivotable relative to the second pivot member about a first rotational axis;

wherein the second pivot member is pivotable relative to the third pivot member about a second rotational axis that is orthogonal to the first rotational axis;

wherein the third pivot member is pivotable relative to the adjacent base member about a third rotational axis that is orthogonal to the second rotational axis; and wherein the first, second and third rotational axes all substantially intersect at a single coincident point of universal rotation thereby permitting the body to rotate in three dimensions relative to the adjacent base member without translating relative to the adjacent base member.

2. The combination of claim 1, wherein each connector further comprises:

a fastener extending from the third pivot element through an aperture in the adjacent base member;

wherein the fastener comprises a shank located within the aperture and a headed end located on the side of the aperture distal the coincident point of universal rotation;

wherein the third rotational axis coincides with the longitudinal axis of the shank; and wherein the shank is rotatable within the aperture.

3. The combination of claim 2, wherein each fastener can be removed from the adjacent base member, thereby permitting struts to be replaced without adjusting the length of the struts or altering the relative positions of the proximal and distal base members.

4. The combination of claim 2, wherein:

the fastener further comprises a threaded end adjacent the shank and distal the headed end;

the third pivot element defines a threaded receptacle in which the threaded end of the fastener can be received;

the edge of the shank adjacent the threaded end is larger than the threaded receptacle, thereby preventing the shank from entering the receptacle; and the axial length of the shank is slightly greater than the axial depth of the aperture, thereby permitting the connecter to rotate about the aperture.

5. The combination of claim 1, wherein the first, second and third pivot members form a U-joint.

6. In combination with an orthopaedic external fixator having proximal and distal base members that can be manipulated translated relative to each other to position a first tissue segment relative to a second tissue segment, a telescopically adjustable strut comprising:

a cylindrical shaft with a hollow axial center;

an externally threaded rod that extends into the axial center of the shaft;

an internally threaded adjustment nut that mates with the external threads of the rod; and, a detent means for maintaining the rotational position of the adjustment nut relative to the shaft;

wherein the adjustment nut is rotatably attached to an end of the shaft through which the rod extends;

wherein rotational axis of the rod is fixed relative to the shaft, whereby rotation of the nut relative to the rod will cause the rod to translate about the axis of the shaft; and, wherein the detent means engages at least once for each revolution of the adjustment nut relative the shaft.

7. The combination of claim 6, wherein:

the shaft includes a first depression adjacent the nut;

the adjustment nut includes a second depression which aligns with the first depression upon each rotation of the adjustment nut relative to the shaft;

the detent means extends from one depression to engage both depressions when the depressions are in alignment; and the second depression of the adjustment nut can be rotated past the first depression of the shaft by applying sufficient torque between the nut and the shaft to compress the detent means into one depression.

8. The combination of claim 7, wherein:

the detent means is contained within the first depression and further comprises a spring and an extension element;

the spring biases the extension element against the shaft, thereby forcing the extension element to engage the second depression when the depressions are in alignment; and a common surface between the extension element and the second depression is at an inclined plane relative to the radial translation of the first depression and relative to the second depression, whereby the locking element will be forced out of the second depression when sufficient torque is applied between the adjustment nut and the shaft to compress the spring.

9. The combination of claim 6 wherein:

the adjustment nut includes an internal radial groove;

the shaft extends inside the adjustment nut and further includes an external radial groove adjacent the internal axial groove of the adjustment nut; and the strut further comprises a snap ring which rests within the axial grooves of both the adjustment nut and the shaft, thereby rotatably attaching the adjustment nut to the shaft.

10. The combination of claim 6, wherein:

the shaft further includes a slot extending along the side of the shaft in the axial direction;

the strut further includes a projection attached to the side of the rod and extending through the slot, whereby axial rotation of the rod relative to the shaft is prevented by the projection;

the projection is externally visible through the slot; and the shaft further comprises graduated marks along the slot, whereby the relative position of the rod and the shaft is indicated by the location of the projection relative to the marks.

11. The combination of claim 6, wherein:

the shaft has an external annular recess;

the strut has an identification band located within said recess extending around more than 180 degrees of the recess;

the identification band is formed of a resilient material stiff enough to secure the identification band on the shaft yet flexible enough to permit removal of the identification band; and the identification band indicates the position of the strut relative to the orthopedic external fixator.

12. The combination of claim 11, wherein the identification band comprises a color unique to the position of the associated strut on the orthopaedic fixator.

13. The combination of claim 6, wherein the threads on the rod and the shaft are pitched such that one or more complete revolution of the nut about the axis of the shaft causes the rod to axially translate one millimeter relative to the shaft.

14. In combination with an orthopaedic external fixator having proximal and distal base members that can be manipulated relative to each other to position a first tissue segment relative to a second tissue segment, a telescopically adjustable strut comprising:

a cylindrical shaft with a hollow axial center;

an externally threaded rod that extends into the axial center of the shaft;

an internally threaded adjustment nut that is rotatably attached to an end of shaft and mates with the external threads of the rod whereby rotation of the nut relative to the rod will cause the rod to translate about the axis of the shaft;

a pair of connectors, one rotatably attaching the proximal end of the strut to the proximal base member and one rotatably attaching the distal end of the strut to the distal base member; and, means for rotating the strut relative to that base member about three rotational axes that substantially intersect at a single coincident point of universal rotation thereby permitting the strut to rotate in three dimensions relative to the adjacent base member without translating relative to the adjacent base member.

15. The combination of claim 14, wherein the rotating means comprises:

a) a first pivot member joined to the adjacent end of the strut;

b) a second pivot member pivotally joined to the first pivot member; and c) a third pivot member pivotally joined to the second pivot member and pivotally joined to the adjacent base member;

wherein the first pivot member is pivotable relative to the second pivot member about a first rotational axis;

wherein the second pivot member is pivotable relative to the third pivot member about a second rotational axis that is orthogonal to the first rotational axis;

wherein the third pivot member is pivotable relative to the adjacent base member about a third rotational axis that is orthogonal to the second rotational axis;

wherein the first, second and third rotational axes all intersect at the coincident point of universal rotation.

16. The combination of claim 14, wherein:

the strut further comprises detent means for holding the rotational position of the adjustment nut relative to the shaft; and the detent means engages at least once for each revolution of the adjustment nut relative to the shaft.

17. The combination of claim 16, wherein:

the detent means can be disengaged by applying a predetermined torque to the adjustment nut relative to the shaft; and the torque required to disengage the detent means is greater than the torque required to rotate the strut about the connector means.

18. The combination of claim 16, wherein:

the shaft includes a first depression adjacent the nut;

the adjustment nut includes a second depression which aligns with the first depression upon each complete rotation of the adjustment nut relative to the shaft;

the detent means extends from one depression to engage both depressions when the depressions are in alignment; and the second depression can be rotated past the first depression by applying sufficient torque between the nut and the shaft to force the detent means into one depression.

19. The combination of claim 18, wherein:

the detent means is secured within the first depression and further comprises a spring and a ball combination in which the spring biases the ball against the shaft, thereby forcing the ball into the second depression when the depressions are in alignment; and the second depression forms an inclined plane relative to the rotation of the nut, whereby the ball is forced out of the second depression when sufficient torque is applied between the nut and the shaft to compress the spring.

20. The combination of claim 14 wherein:

the adjustment nut further includes an internal radial groove;

the shaft further includes an external radial groove adjacent the internal axial groove of the nut; and the strut includes a snap ring which rests within the axial grooves of both the nut and the shaft, thereby rotatably attaching the nut to the shaft.

21. The combination of claim 14, wherein:

the shaft further comprises a slot extending along the side of the shaft in an axial direction; and the strut further comprises a projection attached to the side of the rod and extending through the slot, whereby rotation of the rod relative to the shaft is prevented by the projection;

the projection is externally visible through the slot; and the shaft further comprises graduated marks positioned along the slot, whereby the relative position of the rod and the shaft is indicated by the location of the projection relative to the marks.

22. The combination of claim 14, wherein:

the shaft defines an external annular recess;

the strut has an identification band located within the recess and extending around more than 180 degrees of the recess;

the identification band is formed of a resilient material stiff enough to hold the identification band on the shaft yet flexible enough to permit removal of the identification band; and the identification band indicates the position of the strut relative to the other components of the orthopaedic external fixator.

23. The combination of claim 22, wherein the identification band comprises a color unique to the position of the associated strut.

24. The combination of claim 14, wherein the threads on the rod and the shaft are pitched such that one or more complete revolutions of the adjustment member about the axis of the shaft will cause the rod to translate axially one millimeter relative to the shaft.

* * * * *